United States Patent [19]
Goto et al.

[11] Patent Number: 5,296,454
[45] Date of Patent: Mar. 22, 1994

[54] ACETANILIDE HERBICIDES

[75] Inventors: Toshio Goto; Hidenori Hayakawa; Itsuko Manabe; Akihiko Yanagi, all of Tochigi, Japan

[73] Assignee: Nihon Bayer Agrochem K.K., Tokyo, Japan

[21] Appl. No.: 905,944

[22] Filed: Jun. 26, 1992

[30] Foreign Application Priority Data

Jul. 3, 1991 [JP] Japan .................................. 3-188238
Jul. 9, 1991 [JP] Japan .................................. 3-193647
Sep. 20, 1991 [JP] Japan .................................. 3-268607

[51] Int. Cl.$^5$ .................... A01N 43/08; A01N 43/10; C07D 307/54; C07D 333/24
[52] U.S. Cl. .................................. 504/289; 504/291; 504/294; 504/312; 504/315; 504/336; 549/60; 549/77; 549/472; 549/493; 549/496; 549/551; 558/404; 560/43; 564/182
[58] Field of Search .................... 549/77, 493, 60, 472, 549/496; 71/90, 88; 504/289, 294

[56] References Cited

U.S. PATENT DOCUMENTS

| | | | |
|---|---|---|---|
| 4,453,975 | 6/1989 | Takematsu et al. | 564/182 |
| 4,535,092 | 8/1985 | Hughes | 549/77 |
| 4,685,962 | 8/1987 | Takematsu et al. | 564/170 |

FOREIGN PATENT DOCUMENTS

| | | |
|---|---|---|
| 0061836 | 2/1982 | European Pat. Off. . |
| 00611583 | 2/1982 | European Pat. Off. . |
| 0079191 | 11/1982 | European Pat. Off. . |
| 1921841 | 4/1969 | Fed. Rep. of Germany . |
| 2421897 | 4/1978 | France . |
| 130847 | 1/1984 | Japan . |
| 62-205073 | 9/1987 | Japan .................................. 549/77 |

OTHER PUBLICATIONS

Derwent abstract of JP 205,073 (Sep. 9, 1987).
Derwent abstract of JP 59-076045 (Apr. 28, 1984).
Derwent abstract of JP 59-130,847 (Feb. 27, 1984).
Chemical Abstracts 101: 120,426h p. 684 (1984) abstract of JP 59-76,045 (1984).
J. Pesticide Sci. 13, 19–27 (1988), "Synthesis and Herbicidal Activity of N-Aryl-2-Methyl-2-Arylpropanamides and . . . "
Borgna P. e Coll., Il Farmaco, Ed. Wc.-vol. 31, pp. 284–290 "Preparazione e Studio Dell'Attivita Fitotossica di Anilidi Dell'AC . . . " (1976).
Chemical Abstracts vol. 93, p. 46399, 1980.

Primary Examiner—Richard L. Raymond
Attorney, Agent, or Firm—Sprung Horn Kramer & Woods

[57] ABSTRACT

The invention relates to novel acetanilides of the formula (I)

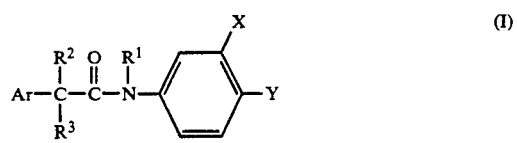

wherein
Ar represents phenyl, furyl or thienyl,
$R^1$ represents hydrogen, $C_{1-5}$-alkyl, $C_{3-6}$-cycloalkyl, $C_{3-6}$-cycloalkyl-methyl, $C_{3-5}$ alkenyl, $C_{3-5}$-alkynyl, $C_{1-3}$-haloalkyl, $C_{3-5}$-epoxyalkyl, $C_{1-3}$-alkoxy-$C_{1-4}$-alkyl, $C_{1-3}$-alkylthio-$C_{1-4}$-alkyl, $C_{1-3}$-alkoxycarbonyl-$C_{1-2}$-alkyl, cyano-$C_{1-3}$-alkyl, or aralkyl
$R^2$ represents hydrogen or $C_{1-3}$-alkyl,
$R^3$ represents hydrogen or $C_{1-3}$-alkyl,
X represents halogen, and
Y represents iso-propyl, tert-butyl, $C_{1-2}$-haloalkyl, $C_{1-2}$-haloalkoxy, $C_{1-2}$-haloalkylthio or $C_{1-2}$-alkylsulfonyl, to processes for their preparation and to their use as herbicides. The invention also relates to novel intermediates and to processes for their preparation.

10 Claims, No Drawings

ACETANILIDE HERBICIDES

The present invention relates to novel acetanilides, to processes for their preparation and to their use as herbicides. The invention also relates to novel intermediates and to processes for their preparation.

It ihas already been disclosed that certain α,α-diphenyl acetic acids are useful as herbicides (see Japanese Laid-Open Patent Application Nos. 144203/1982 (EP-O 0 611 583), 76045/1984 (CA 101/130426), 130847/1984, 136546/1985 (EP-O 0 147 788) and 53184/1988 (U.S. Pat. No. 4,685,962), and certain acylanilides are useful as an anti-testosterone (see Japanese Laid-Open Patent Application No. 85862/1983 (EP-O 079 191).

There have now been found novel acetanilides of the formula (I)

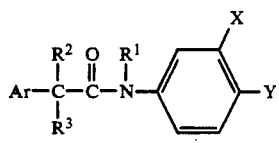

(I)

wherein

Ar represents phenyl, furyl or thienyl, $R^1$ represents hydrogen, $C_{1-5}$-alkyl, $C_{3-6}$-cycloalkyl, $C_{3-6}$-cycloalkyl-methyl, $C_{3-5}$ alkenyl, $C_{3-5}$-alkynyl, $C_{1-3}$-haloalkyl, $C_{3-5}$-epoxyalkyl, $C_{1-3}$-alkoxy-$C_{1-4}$-alkyl, $C_{1-3}$-alkylthio-$C_{1-4}$-alkyl, $C_{1-3}$-alkoxycarbonyl-$C_{1-2}$-alkyl, cyano-$C_{1-3}$-alkyl, or aralkyl, $R^2$ represents hydrogen or $C_{1-3}$-alkyl, $R^3$ represents hydrogen or $C_{1-3}$-alkyl, X represents halogen, and Y represents iso-propyl, tert-butyl, $C_{1-2}$-haloalkyl, $C_{1-2}$-haloalkoxy, $C_{1-2}$-haloalkylthio or $C_{1-2}$-alkylsulfonyl.

Acetanilides of the formula (I) are obtained when a) in the case where $R^1$ represents hydrogen: anilines of the formula (II)

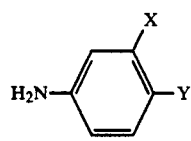

(II)

wherein X and Y have the above mentioned meanings, are reacted with compounds of the formula (III)

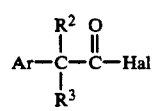

(III)

wherein Ar, $R^2$ and $R^3$ have the above mentioned meanings, and Hal is chlorine, bromine or iodine, in the presence of inert solvents and, if appropriate, in the presence of acid binders, or b) in the case where $R^1$ represents the above definition other than hydrogen, then $R^1$ is replaced by $R^4$, $R^4$ representing those definitions of $R^1$ other than hydrogen:

acetanilides of the formula (IV)

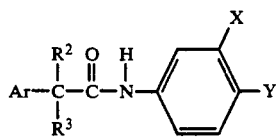

(IV)

wherein $R^2$, $R^3$, Ar, X and Y have the above mentioned meanings, are reacted with compounds of the formula (V)

$$Hal-R^4 \quad (V)$$

wherein $R^4$ and Hal have the above mentioned meanings, in the presence of inert solvents and, if appropriate, in the presence of acid binders.

The novel acetanilides of the formula (I) exhibit powerful herbicidal properties.

Surprisingly, the acetanilides according to the invention exhibit a substantially stronger selective herbicidal action than those known from the prior art, for instance, the aforementioned Japanese Laid-Open Patent Application Nos. 144203/1982, 76045/1984, 130847/1984, 136546/1985 and 53184/1988.

Among the acetanilides according to the invention of the formula (I), the preferred compounds are those in which Ar represents phenyl, 2-furyl, 3-furyl, 2-thienyl or 3-thienyl;

$R^1$ represents hydrogen, $C_{1-3}$-alkyl, cyclopropyl, cyclopentyl, cyclohexyl, cyclohexylmethyl, cyclopropylmethyl, allyl, butenyl, propargyl, butynyl, halomethyl, 2,3-epoxypropyl, $C_{1-2}$-alkoxy-$C_{1-2}$-alkyl, $C_{1-2}$-alkylthio-$C_{1-2}$-alkyl, $C_{1-2}$-alkoxycarbonyl-$C_{1-2}$-alkyl, cyano-$C_{1-2}$-alkyl, or halogen-substituted benzyl and the halogen-atoms are selected from the group consisting of fluorine, chlorine and bromine, $R^2$ represents hydrogen, methyl or ethyl, $R^3$ represents hydrogen, methyl or ethyl, X represents fluorine, chlorine or bromine, and Y represents iso-propyl, tert-butyl, $C_{1-2}$-fluoroalkyl, $C_{1-2}$-fluoro-alkylthio or $C_{1-2}$-fluorosulfonyl, with up to five fluorine atoms.

Very particularly preferred acetanilides of the formula (I) are those in which

Ar represents phenyl, 2-furyl, 2-thienyl or 3-thienyl, $R^1$ represents hydrogen, methyl, ethyl, n-propyl, iso-propyl, cyclopropyl, allyl, propargyl, chloromethyl, dichloromethyl, trichloromethyl, 2,3-epoxypropyl, methoxymethyl, ethoxymethyl, methoxyethyl, methylthiomethyl, methylthioethyl, ethylthiomethyl or cyanomethyl, $R^2$ represents hydrogen or methyl, $R^3$ represents hydrogen or methyl, X represents fluorine, chlorine or bromine, and Y represents iso-propyl, tert-butyl, difluoromethyl, trifluoromethyl, difluoromethoxy, trifluoromethoxy, 1,1,2,2-tetrafluoroethoxy, difluoromethylthio, trifluoromethylthio or 1,1,2,2-tetrafluoroethylthio.

As single disclosed compounds of the formula (I) according to the invention may be mentioned:

2-methyl-2-phenylpropionic acid (3-chloro-4-trifluoromethyl) anilide, 2-phenylpropionic acid (3-chloro-4-trifluoromethyl) anilide, 2-methyl-2-phenylpropionic acid (3-chloro-4-trifluoromethoxy) anilide,
2-phenylpropionic acid (3-chloro-4-trifluoromethoxy) anilide,
2-phenylacetic acid (3-chloro-4-trifluoromethyl) anilide,
2-methyl-2-phenylpropionic acid (3-chloro-4-trifluoromethylthio) anilide,
2-phenylpropionic acid (3-chloro-4-trifluoromethylthio) anilide,
2-phenylacetic acid (3-chloro-4-trifluoromethoxy) anilide,
2-methyl-2-phenylpropionic acid (3-chloro-4-difluoromethyl) anilide,
2-phenylpropionic acid (3-chloro-4-difluoromethyl) anilide,
2-methyl-2-phenylpropionic acid (3-chloro-4-difluoromethoxy) anilide,
2-phenylpropionic acid (3-chloro-4-difluoromethoxy) anilide,
2-phenylacetic acid (3-chloro-4-difluoromethyl) anilide,
2-methyl-2-phenylpropionic acid (3-chloro-4-difluoromethylthio) anilide,
2-phenylpropionic acid (3-chloro-4-difluoromethylthio) anilide,
2-phenylacetic acid (3-chloro-4-difluoromethoxy) anilide,
2-methyl-2-phenylpropionic acid (3-fluoro-4-trifluoromethyl) anilide,
2-phenylpropionic acid (3-fluoro-4-trifluoromethyl) anilide,
2-methyl-2-phenylpropionic acid (3-fluoro-4-trifluoromethoxy) anilide,
2-phenylpropionic acid (3-fluoro-4-trifluoromethoxy) anilide,
2-phenylacetic acid (3-fluoro-4-trifluoromethyl) anilide,
2-methyl-2-phenylpropionic acid (3-fluoro-4-trifluoromethylthio) anilide,
2-phenylpropionic acid (3-fluoro-4-trifluoromethylthio) anilide,
2-phenylacetic acid (3-fluoro-4-trifluoromethoxy) anilide,
2-methyl-2-phenylpropionic acid (3-fluoro-4-difluoromethyl) anilide,
2-phenylpropionic acid (3-fluoro-4-difluoromethyl) anilide,
2-methyl-2-phenylpropionic acid (3-fluoro-4-difluoromethoxy) anilide,
2-phenylpropionic acid (3-fluoro-4-difluoromethoxy) anilide,
2-phenylacetic acid (3-fluoro-4-difluoromethyl) anilide,
2-methyl-2-phenylpropionic acid (3-fluoro-4-difluoromethylthio) anilide,
2-phenylpropionic acid (3-fluoro-4-difluoromethylthio) anilide,
2-phenylacetic acid (3-fluoro-4-difluoromethoxy) anilide,
2-(2-furyl)acetic acid (3-chloro-4-trifluoromethoxy) anilide,
2-(2-furyl)acetic acid (3-chloro-4-trifluoromethyl) anilide,
2-methyl-2-(2-furyl) propionic acid (3-chloro-4-difluoromethyl) anilide,
2-methyl-2-(2-furyl) propionic acid (3-chloro-4-trifluoromethyl) anilide,
2-(2-furyl)propionic acid (3-chloro-4-difluoromethyl) anilide,
2-(2-furyl)propionic acid (3-chloro-4-trifluoromethyl) anilide,
2-methyl-2-(2-furyl)propionic acid (3-chloro-4-difluoromethoxy) anilide,
2-(2-furyl)propionic acid (3-chloro-4-difluoromethoxy) anilide,
2-(2-furyl)aceticacid (3-chloro-4-difluoromethyl) anilide,
2-methyl-2-(2-furyl)propionic acid (3-chloro-4-difluoromethylthio) anilide,
2-(2-furyl)propionic acid (3-chloro-4-difluoromethylthio) anilide,
2-(2-furyl)acetic acid (3-chloro-4-difluoromethoxy) anilide,
2-methyl-2-(2-furyl)propionic acid (3-fluoro-4-trifluoromethyl) anilide,
2-(2-furyl)propionic acid (3-fluoro-4-trifluoromethyl) anilide,
2-methyl-2-(2-furyl)propionic acid-(3-fluoro-4-trifluoromethoxy)anilide,
2-(2-furyl)propionic acid (3-fluoro-4-trifluoromethoxy) anilide,
2-(2-furyl)acetic acid (3-fluoro-4-trifluoromethyl) anilide,
2-methyl-2-(2-furyl)propionic acid (3-fluoro-4-trifluoromethylthio) anilide,
2-(2-furyl)acetic acid (3-chloro-4-trifluoromethoxy) anilide,
2-methyl-2-(3-furyl)propionic acid (3-chloro-4-difluoromethyl) anilide,
2-(3-furyl)propionic acid (3-chloro-4-difluoromethoxy) anilide,
2-methyl-2-(3-furyl)propionic acid (3-chloro-4-difluoromethoxy) anilide,
2-(3-furyl)propionic acid (3-chloro-4-difluoromethoxy) anilide,
2-(3-furyl)acetic acid (3-chloro-4-difluoromethyl) anilide,
2-methyl-2-(3-furyl)propionic acid (3-chloro-4-difluoromethylthio) anilide,
2-(3-furyl)propionic acid (3-chloro-4-difluoromethylthio) anilide,
2-(3-furyl)acetic acid (3-chloro-4-difluoromethoxy) anilide,
2-methyl-2-(3-furyl)propionic acid (3-fluoro-4-trifluoromethyl) anilide,
2-(3-furyl)propionic acid (3-fluoro-4-trifluoromethyl) anilide,
2-methyl-2-(3-furyl)propionic acid (3-fluoro-4-trifluoromethoxy) anilide,
2-(3-furyl)propionic acid (3-fluoro-4-trifluoromethoxy) anilide,
2-(3-furyl) acetic acid (3-fluoro-4-trifluoromethyl) anilide,
2-methyl-2-(3-furyl)propionic acid (3-fluoro-4-trifluoromethylthio) anilide,
2-(2-thienyl)acetic acid (3-chloro-4-trifluoromethoxy) anilide,
2-(2-thienyl)acetic acid (3-chloro-4-trifluoromethyl) anilide
2-methyl-2-(2-thienyl)propionic acid (3-chloro-4-difluoromethyl) anilide,
2-methyl-2-(2-thienyl)propionic acid (3-chloro-4-trifluoromethyl) anilide,
2-(2-thienyl)propionic acid (3-chloro-4-difluoromethyl) anilide, 2-methyl-2-(2-thienyl)propionic acid (3-chloro-4-difluoromethoxy) anilide,
2-(2-thienyl)propionic acid (3-chloro-4-difluoromethoxy) anilide,
2-(2-thienyl)acetic acid (3-chloro-4-difluoromethyl) anilide,
2-methyl-2-(2-thienyl)propionic acid (3-chloro-4-difluoromethylthio) anilide,
2-(2-thienyl)propionic acid (3-chloro-4-difluoromethylthio) anilide,
2-(2-thienyl)acetic acid (3-chloro-4-difluoromethoxy) anilide,
2-methyl-2-(2-thienyl)propionic acid (3-fluoro -4-trifluoromethyl) anilide,
2-(2-thienyl)propionic acid (3-fluoro-4-trifluoromethyl) anilide,
2-methyl-2-(2-thienyl)propionic acid (3-fluoro-4-trifluoromethoxy) anilide,
2-(2-thienyl) propionic acid (3-fluoro-4-trifluoromethoxy) anilide,
2-(2-thienyl)acetic acid (3-chloro-4-trifluoromethyl) anilide,
2-methyl-2-(3-thienyl)propionic acid (3-chloro-4-difluoromethyl) anilide,
2-(3-thienyl)propionic acid (3-chloro-4-difluoromethyl) anilide,
2-methyl-2-(3-thienyl)propionic acid (3-chloro-4-difluoromethoxy) anilide,
2-(3-thienyl)propionic acid (3-chloro-4-difluoromethoxy) anilide,
2-(3-thienyl)acetic acid (3-chloro-4-difluoromethyl) anilide,
2-methyl-2-(3-thienyl)propionic acid (3-chloro-4-difluoromethylthio) anilide,
2-(3-thienyl)propionic acid (3-chloro-4-difluoromethylthio) anilide,
2-(3-thienyl)acetic acid (3-chloro-4-difluoromethoxy) anilide,
2-(3-thienyl)acetic acid (3-chloro-4-trifluoromethoxy) anilide,
2-methyl-2-(3-thienyl)propionic acid (3-fluoro-4-trifluoromethyl) anilide,
2-(3-thienyl)propionic acid (3-fluoro-4-trifluoromethyl) anilide,
2-(3-thienyl)propionic acid (3-chloro-4-trifluoromethyl) anilide,
2-methyl-2-(3-thienyl)propionic acid (3-fluoro-4-trifluoromethoxy) anilide,
2-(3-thienyl)propionic acid (3-fluoro-4-trifluoromethoxy) anilide,
2-(3-thienyl)propionic acid (3-fluoro-4-trifluoromethyl) anilide,
2-(3-thienyl)acetic acid (3-fluoro-4-trifluoromethyl) anilide,
2-methyl-2-(3-thienyl)propionic acid (3-fluoro-4-trifluoromethylthio) anilide,
2-(2-thienyl)acetic acid (3-chloro-4-iso-propyl) anilide,
2-(2-thienyl)propionic acid (3-chloro-4-iso-propyl) anilide,
2-methyl-(2-thienyl)propionic acid (3-chloro-4-iso-propyl) anilide,
2-(3-thienyl)acetic acid (3-chloro-4-iso-propyl) anilide,
2-(3-thienyl)propionic acid (3-chloro-4-iso-propyl) anilide, and
2-methyl-(3-thienyl)propionic acid (3-chloro-4-iso-propyl) anilide.

If, for example, in the process a) 3-chloro-4-trifluoromethyl aniline and 2-methyl-2-phenyl propionic acid chloride are used as starting materials, the course of the reaction can be represented by the following equation:

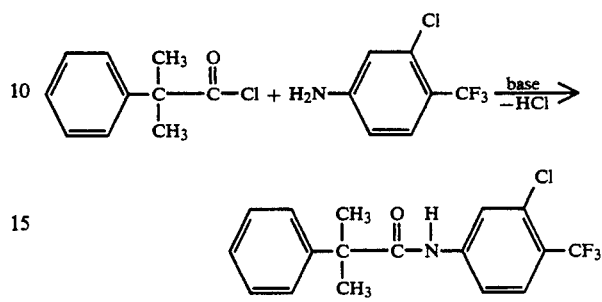

If, for example in the process b) 2-methyl-2-(2-thienyl) propionic acid-(3-chloro-4-trifluoromethyl-anilide) and propargly bromide are used as starting materials, the course of the reaction can be represented by the following equation:

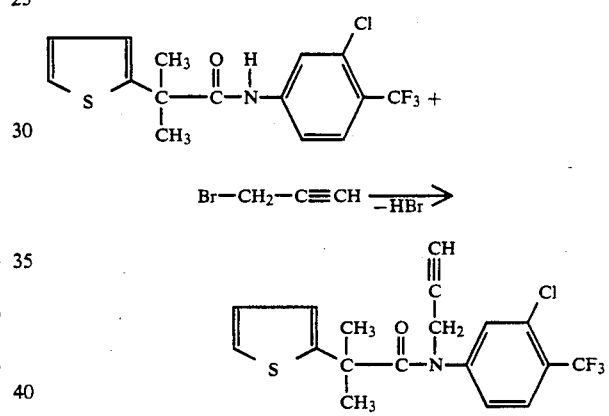

In the process a), the starting compounds of the formula (II) mean compounds based on the above definitions of X and Y, preferably compounds based on the above preferred definitions.

The anilines of the formula (II) are described, for example, in Japanese Laid-open Patent Application No. 28667/1990. A specific example of the anilines of the formula (II) are
3-chloro-4-trifluoromethylaniline
3-chloro-4-trifluoromethoxyaniline
3-chloro-4-trifluoromethylthioaniline
3-chloro-4-iso-propylaniline, and
3-bromo-4-trifluoromethoxyaniline.

In the process a), the starting compounds of the formula (III) means compounds based on the above definitions of Ar, Hal, $R^2$ and $R^3$, preferably compounds based on the above preferred definitions, Hal preferably means chlorine and bromine.

The compounds of the formula (III) can be obtained, when compounds of the formula (VI)

(VI)

wherein Ar, $R^2$ and $R^3$ have the above mentioned meanings, are halogenated with chlorine or bromine in the presence of inert solvents.

In the case where Ar represents phenyl or furyl, then the compounds of the formula (III) are well known. Specific examples of those compounds are 2-phenylacetic acid chloride,
2-phenylpropionic acid chloride,
2-phenyl-2-methylpropionic acid chloride,
2-(2-furyl)acetic acid chloride,
2-(2-furyl)propionic acid chloride, and
2-(2-furyl)-2-methylpropionic acid chloride.

When the compounds of the formula (VI) are (2-(2-thienyl) acetic acid derivatives (VIa),

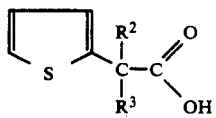
(VIa)

they can be obtained by processes which were disclosed by "Ann. Chem.", 7, 303-37, (1962), "Bull. Soc. Chim.", 847, (1949), "J.A.C.S.", 73.2779-81, (1951), "Bull. Soc. Chim.", 1820-2, (1961), and "J.O.C.", 23, 1989-92. When $R^2$ and $R^3$ represent different alkyl substituents, they are novel compounds which cannot be obtained by the processes that were disclosed by the above mentioned literature but can be obtained by the process mentioned hereinafter.

When the compounds of the formula (VI) are 2-(3-thienyl) acetic acid derivatives (VIb)

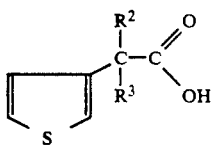
(VIb)

they can be obtained by processes which were disclosed by Spanish Patent Nos. 487840 and 504690. These processes give rise to a number of disadvantages like difficulties in synthesizing the 2-(3-thienyl) acetic acid derivatives and hard-to-dispose heavy metal oxides.

Further, when $R^2$ and $R^3$ represent the same alkyl groups, they are also novel compounds which can be obtained with high yields, according to the process mentioned hereinafter.

In the case where Ar is thienyl, the compounds of the formula (VI) are obtained when c) compounds of the general formula (VII)

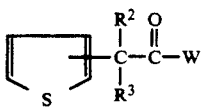
(VII)

wherein $R^2$ and $R^3$ have the above mentioned meanings, W is cyano, methoxycarbonyl or ethoxycarbonyl are hydrolyzed in the presence of inert solvents.

Compounds of the formula (VII) are obtained when d) in the case where $R^2$ and $R^3$ represent the same alkyl; compounds of the formula (VIII)

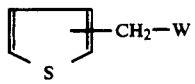
(VIII)

wherein W has the above mentioned meaning, are reacted with compounds of the formula (IX)

Hal—alk (IX)

wherein Hal has the above mentioned meaning and alk is $C_{1-3}$alkyl, or the compounds of the formula (X)

$(alk)_2SO_4$ (X)

wherein alk has the above mentioned meaning, in the presence of inert solvents, e) in the case where one of $R^2$ and $R^3$ represents hydrogen, while the other represents alkyl;

the compounds of the formula (VIII) are reacted with butyl lithium, lithium diisopropylamide or the like, and after lithiation, the reaction products are reacted with $C_{1-3}$alkyl iodide in the presence of inert solvents.

f) In the case where $R^2$ and $R^3$ represent the same or different alkyl;

compounds of the formula (XI)

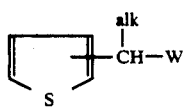
(XI)

wherein alk and W have the above mentioned meaning, are reacted with the compounds of the formula (IX), in the presence of inert solvents, if appropriate in the presence of acid binders.

In the process d), the starting compounds of the formula (VIII) are known compounds. Specific examples of the formula (VIII) are 3-thiophene acetic acid methyl ester, and
2-thiophene acetic acid ethyl ester.

In the process f), the starting materials of the formula (XI) can be obtained according to the above mentioned process e). As the example of the compounds of the formula (XI), there may be mentioned.

2-(3-thienyl)propionic acid methyl ester.

In the process b), the starting compounds of the formula (IV) means compounds based on the above definitions of Ar, X, Y, $R^2$ and $R^3$, preferably compounds based on the preferred definitions.

In the process b), the starting compounds of the formula (IV) can be obtained according to the above mentioned process a).

As the examples of the compounds of the formula (IV), there may be mentioned:

2-methyl-2-(2-thienyl)propionic acid (3-chloro-4-trifluoromethyl)anilide,
2-methyl-2-(3-thienyl)propionic acid (3-chloro-4-trifluoromethyl)anilide,
2-(3-thienyl)propionic acid (3-chloro-4-trifluoromethyl)anilide, and
2-thienylacetic acid (3-chloro-4-trifluoromethyl)anilide.

In the process b), the starting compounds of the formula (V) means compounds based on the above defitions of $R^4$, preferably compounds based on the above preferred definitions of $R^1$ except for hydrogen.

In the process b), the starting materials of the formula (V) are well known, as the examples of the compounds of the formula (V), there may be mentioned:
propargylbromide, n-propylbromide, allylbromide, cyclopropylbromide, cyclopropylmethylbromide, bromoacetonitrile, methoxymethylchloride, methoxyethylchloride,
methylthiomethylchloride, bromoethyl acetic acid, benzylbromide, and so on:

In carrying out the process a) mentioned above, use may be made, as suitable diluent, of any inert solvent.

Examples of such diluents are aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, 1,2-dichloroethane, ethylene chloride, chlorobenzene, dichlorobenzene, and the like; ethers such as diethyl ether, methyl ethyl ether, di-isopropyl ether, di-butyl ether, dimethoxyethane (DME), dioxane, tetrahydrofurane (THF) and the like; ketones such as acetone methylethyl ketone (MEK), methyl-iso-propyl ketone, methyl-iso-butyl ketone (MIBK) and the like; nitriles such as acetonitrile, propionitrile, and the like; and bases, for example, such as pyridine.

the above mentioned process a) is carried out preferably in the presence of acid binder and as acid binder may be mentioned inorganic bases such as, for example, carbonate, and bicarbonate of alkalimetals, such as sodium hydrogen carbonate, potassium hydrogen carbonate, sodium carbonate and potassium carbonate. As organic bases may be mentioned tertiary amines such as dialkylamino anilines and pyridines such as, for example, triethylamine, tributylamine, 1,1,4,4-tetramethylethylenediamine (TDMEDA), N,N-dimethylaniline, N,N-diethylaniline, pyridine, 4-dimethylamino pyridine (DMAP), 1,4-diazabicyclo[2,2,2]octane (DABCO) and 1,8-diazabicyclo[5,4,0]undec-7-ene (DBU).

In the above mentioned process a), the reaction temperature can be varied within a substantially wide range. In general, the reaction is carried out at a temperature from $-10°$ C. to $200°$ C., preferably from $0°$ C. to $150°$ C.

Further, the reaction is preferably carried out under normal pressure, but a higher or reduced pressure may also be used.

In carrying out the process a) the desired compounds of the formula (I) can be obtained by reacting about 0.5 to 1.5 mols of the compounds of the formula (III) in a diluent such as toluene with 1 mol of the compounds of the formula (II) in the presence of a base such as triethylamine.

In carrying out the process b) mentioned above, use may be made, as suitable diluent, of any inert solvent.

Examples of such diluents are aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene, and the like; ethers such as diethyl ether, methyl ethyl ether, di-isopropyl ether, dibutyl ether, dimethoxyethane (DMF), dioxane, tetrahydrofuran (THF) diethyleneglycol dimethylether (DGM) and the like; ketones such as acetone methylethyl ketone (MEK), methyl-iso-propyl ketone, methyl-iso-butyl ketone (MIBK) and the like; nitriles such as acetonitrile, propionitrile, and the like; acid amides such as dimethyl formamide (DMF), dimethyl acetamide (DMA) and the like; and sulfones and sufoxides such as dimethyl sulfoxide (DMSO), sulfolane and the like.

The above mentioned process b) is carried out preferably in the presence of acid binder and as acid binder may be mentioned inorganic bases such as, for example, hydride, carbonate, bicarbonate and alcoholate of alkalimetals such as, for example, sodium hydride, potassium hydride, sodium hydrogen carbonate, potassium hydrogen carbonate, sodium carbonate, potassium carbonate, sodium methoxide, sodium ethoxide, and potassium tert-butoxide.

In the above mentioned process b), the reaction temperature can be varied within a substantially wide range. In general, the reaction is carried out at a temperature from $-30°$ C. to $200°$ C., preferably from $-10°$ C. to $150°$ C. Further, the above mentioned process b) is carried out under normal pressure, but a higher or reduced pressure may also be used.

In carrying out the process b) the desired compounds of the formula (I) according to the present invention can be obtained by reacting about 1.0 to 2.0 mol amount of the compounds of the formula (V) in a diluent such as toluene with 1 mol of the compound of the formula (IV) in the presence of a base such as sodium hydride.

The active compounds according to the invention can be used as defoliants, desiccants, agents for destroying broad-leaved plants and, especially, as weedkillers. By weeds, in the broadest sense, there are to be understood all plants which grow in locations where they are undersired. Whether the substances according to the invention act as total or selective herbicides depends essentially on the amount used.

The active compounds according to the invention can be used, for example, in connection with the following plants;

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Licopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Isochaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharaum, Ananas, Asparagus and Allium.

However, the use of the active compounds according to the invention is in no way restrictred to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquefied solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyformamide and dimethylsulphoxide, as well as water. By liquefied gaseous diluents or carriers are meant liquids which would be gaseous at normal temperature and under normal pressure, for example, aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese boron, copper, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of the active compound used can vary within a substantial range. It depends essentially on the nature of the desired effect. In general, the amounts used are between 0.01 and 10 kg of active compound per hectare of soil surface, preferably between 0.1 and 1 kg per ha.

The preparation and use of the active compounds according to the invention can be seen from the following examples.

PREPARATION EXAMPLES

Example 1

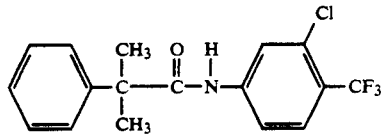

A solution of 3-chloro-4-trifluoromethylaniline (0.98 g), and triethylamine (1.01 g) in toluene (30 ml) was added dropwise to a solution of 2-methyl-2-phenylpropionic acid chloride (1.10 g in 10 ml toluene) at 0° C. When the addition was completed, the reaction mixture was refluxed under heating for two hours. Then, the mixture was concentrated under reduced pressure, followed by addition of water thereto and extraction with ether. The combined organic layers were dried over anhydrous magnesium sulphate, filtered and the ether was removed under reduced pressure. The residue thus obtained was recrystallized from hexane to obtain colorless crystals of 2-methyl-2-phenylpropionic acid (3-chloro-4-trifluoromethyl)aniline (1.47 g). mp 99°-103° C.

Example 2

A solution of 3-chloro-4-trifluoromethylaniline (2.25 g) in toluene (20 ml) was added to a solution (10 ml) of 2-methyl-2-phenylpropionic acid chloride (1.83 g) in toluene (10 ml) at 0° C. followed by a one-hour refluxing under heating. After the reaction was allowed to cool to room temperature, the mixture was treated in a similar manner as described in Example 1 to obtain 2-methyl-2-phenylpropionic acid (3-chloro-4-trifluoromethyl)anilide (3.28 g).

Example 3

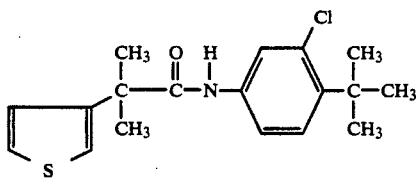

A solution of 3-chloro-4-tert-butylaniline (0.92 g) in toluene (10 ml) was added dropwise to a toluene solution (10 ml) of 2-methyl-2-(3-thienyl)propionic acid chloride (1.04 g) at room temperature. After the addition was completed, the reaction mixture was refluxed under heating for one hour. Then the toluene was distilled off under reduced pressure, and water was added to the residue which was extracted with 2 portions of ether (30 ml). The combined ether phases were dried over anhydrous magnesium sulphate, filtered and the ether was removed under reduced pressure. The residue thus obtained was recrystallized from hexane to obtain 2-methyl-2-(3-thienyl)propionic acid (4-tert-butyl-3-chloro)anilide (1.48 g) with mp 85°-88° C.

Example 4

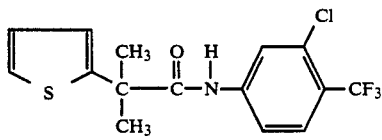

A solution of 3-chloro-4-trifluoromethylaniline (19.56 g), and triethylamine (12.4 g) in toluene (100 ml) was added dropwise to a solution of 2-methyl-2-(2-thienyl)-propionic acid chloride (19.81 g) in toluene at room temperature, under stirring. After the completion of the addition, the reaction mixture was allowed to reflux for thirty minutes. Then the reaction mixture was cooled to room temperature and was washed with water. Thereafter the organic layer was dried over anhydrous magnesium sulfate, filtered and the solvent was removed under reduced pressure, followed by recrystallization of the residue from hexane to obtain colorless crystals of 2-methyl-2-(2-thienyl)propionic acid (3-chloro-4-trifluoromethyl)anilide (31.42 g) with mp 73°-75.5° C.

Example 5

A solution of 3-chloro-4-trifluoromethylaniline (2.25 g) in toluene was added to 2-methyl-2-(2-thienyl)propionic acid chloride (1.89 g) at room temperature, followed by one-hour refluxing under heating. After the reaction, the mixture was treated as described in Example 4 so as to obtain 3.38 g 2-methyl-2-(2-thienyl)propionic acid (3-chloro-4-trifluoromethyl)anilide.

Example 6

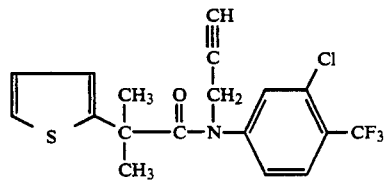

A mixture of 60% sodium hydride in oil (0.30 g) was washed with anhydrous tetrahydrofuran and, after the oil content had been removed, it was suspended in THF (30 ml). To this suspension 2-methyl-2-(2-thienyl)propionic acid (3-chloro-4-trifluoromethyl)anilide (1.74 g) was added portionwise, effecting the metallization and then propargyl bromide (1.19 g) was added. Then the mixture was allowed to reflux for three hours. When the reaction mixture was cooled to room temperature again, a small amount of methanol and then acetic acid were added to the mixture so as to decompose the unreacted sodium hydride, followed by the removal of the solvent under reduced pressure.

Water was added to the residue which was then extracted with dichloromethane, followed by drying over anhydrous magnesium sulfate.

After the solvent had been distilled off under reduced pressure, the residue was purified by silicagel column chromatography (ether eluent) to obtain 1.73 g of oily 2-methyl-2-(2-thienyl)propionic acid N-propargyl-(3-chloro-4-trifluoromethyl)anilide $n_D^{20}$ 1.5424

Table 1 shows the compounds of the invention which may be obtained by the same method as above.

TABLE 1

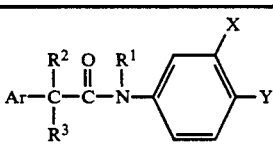

| No | X | Y | R$^1$ | R$^2$ | R$^3$ | Ar | nD or mp |
|---|---|---|---|---|---|---|---|
| 1 | Cl | CF$_3$ | H | H | H | 2-thienyl | 132-133° C. |
| 2 | Cl | OCF$_3$ | H | H | H | 2-thienyl | 102-103° C. |
| 3 | Cl | SCF$_3$ | H | H | H | 2-thienyl | 123-125° C. |
| 4 | Cl | CF$_3$ | H | CH$_3$ | H | 2-thienyl | 82-92° C. |
| 5 | Cl | OCF$_3$ | H | CH$_3$ | H | 2-thienyl | 81-82° C. |
| 6 | Cl | SCF$_3$ | H | CH$_3$ | H | 2-thienyl | 106-114° C. |
| 7 | Cl | CF$_3$ | H | CH$_3$ | CH$_3$ | 2-thienyl | 73-75.5° C. |
| 8 | Cl | OCF$_3$ | H | CH$_3$ | CH$_3$ | 2-thienyl | 63-66° C. |
| 9 | Cl | SCF$_3$ | H | CH$_3$ | CH$_3$ | 2-thienyl | 75-76° C. |
| 10 | Cl | CF$_3$ | H | CH$_3$ | C$_2$H$_5$ | 2-thienyl | 83-86° C. |
| 11 | Cl | OCF$_3$ | H | CH$_3$ | C$_2$H$_5$ | 2-thienyl | 71-72.5° C. |

TABLE 1-continued $$\text{Ar}-\underset{\underset{R^3}{|}}{\overset{\overset{R^2}{|}}{C}}-\underset{}{\overset{\overset{O}{\|}}{C}}-\underset{}{\overset{R^1}{N}}-\text{C}_6\text{H}_3(X)(Y)$$

| No | X | Y | R¹ | R² | R³ | Ar | nD or mp |
|----|---|---|----|----|----|----|----------|
| 12 | Cl | CF₃ | H | C₂H₅ | H | 2-thienyl | 108–109.5° C. |
| 13 | Cl | CF₃ | —CH₂C≡CH | H | H | 2-thienyl | $n_D^{20}$1.5433 |
| 14 | Cl | CF₃ | —CH₂C≡CH | CH₃ | H | 2-thienyl | |
| 15 | Cl | CF₃ | CH₃ | CH₃ | CH₃ | 2-thienyl | |
| 16 | Cl | CF₃ | C₂H₅ | CH₃ | CH₃ | 2-thienyl | $n_D^{20}$1.5350 |
| 17 | Cl | CF₃ | CH₂CH₂CH₃ | CH₃ | CH₃ | 2-thienyl | |
| 18 | Cl | CF₃ | CH(CH₃)₂ | CH₃ | CH₃ | 2-thienyl | |
| 19 | Cl | CF₃ | cyclopropyl | CH₃ | CH₃ | 2-thienyl | |
| 20 | Cl | CF₃ | cyclopentyl | CH₃ | CH₃ | 2-thienyl | |
| 21 | Cl | CF₃ | cyclohexyl | CH₃ | CH₃ | 2-thienyl | |
| 22 | Cl | CF₃ | —CH₂-cyclopropyl | CH₃ | CH₃ | 2-thienyl | $n_D^{20}$1.5433 |
| 23 | Cl | CF₃ | —CH₂-cyclohexyl | CH₃ | CH₃ | 2-thienyl | |
| 24 | Cl | CF₃ | —CH₂CH=CH₂ | CH₃ | CH₃ | 2-thienyl | |
| 25 | Cl | CF₃ | —CH₂C≡CH | CH₃ | CH₃ | 2-thienyl | $n_D^{20}$1.5424 |
| 26 | Cl | CF₃ | CH₂Cl | CH₃ | CH₃ | 2-thienyl | |
| 27 | Cl | CF₃ | CH₂CH₂Cl | CH₃ | CH₃ | 2-thienyl | |
| 28 | Cl | CF₃ | CH₂CF₃ | CH₃ | CH₃ | 2-thienyl | |
| 29 | Cl | CF₃ | —CH₂CH(O)CH₂ (epoxide) | CH₃ | CH₃ | 2-thienyl | $n_D^{20}$1.5438 |
| 30 | Cl | CF₃ | CH₂OCH₃ | CH₃ | CH₃ | 2-thienyl | $n_D^{20}$1.5361 |
| 31 | Cl | CF₃ | CH₂OCH₂CH₃ | CH₃ | CH₃ | 2-thienyl | |
| 32 | Cl | CF₃ | CH₂CH₂OCH₃ | CH₃ | CH₃ | 2-thienyl | |
| 33 | Cl | CF₃ | CH₂CH₂OCH₂CH₃ | CH₃ | CH₃ | 2-thienyl | |
| 34 | Cl | CF₃ | CH₂SCH₃ | CH₃ | CH₃ | 2-thienyl | |
| 35 | Cl | CF₃ | CH₂SCH₂CH₃ | CH₃ | CH₃ | 2-thienyl | |
| 36 | Cl | CF₃ | CH₂CH₂SCH₃ | CH₃ | CH₃ | 2-thienyl | |
| 37 | Cl | CF₃ | CH₂CO₂CH₃ | CH₃ | CH₃ | 2-thienyl | |
| 38 | Cl | CF₃ | CH₂CO₂CH₂CH₃ | CH₃ | CH₃ | 2-thienyl | $n_D^{20}$1.5429 |
| 39 | Cl | CF₃ | —CH(CH₃)CO₂CH₃ | CH₃ | CH₃ | 2-thienyl | |
| 40 | Cl | CF₃ | CH₂CN | CH₃ | CH₃ | 2-thienyl | |
| 41 | Cl | CF₃ | —CH₂-phenyl | CH₃ | CH₃ | 2-thienyl | $n_D^{20}$1.5591 |
| 42 | Cl | CF₃ | —CH₂-(4-Cl-phenyl) | CH₃ | CH₃ | 2-thienyl | |
| 43 | Cl | CHF₂ | H | CH₃ | CH₃ | 2-thienyl | |
| 44 | F | CF₃ | H | CH₃ | CH₃ | 2-thienyl | |

TABLE 1-continued

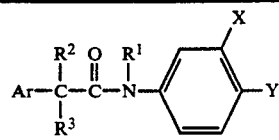

| No | X | Y | R¹ | R² | R³ | Ar | nD or mp |
|---|---|---|---|---|---|---|---|
| 45 | Cl | OCHF$_2$ | H | CH$_3$ | CH$_3$ | 2-thienyl | $n_D^{20}$1.5606 |
| 46 | Cl | SCHF$_2$ | H | CH$_3$ | CH$_3$ | 2-thienyl | |
| 47 | F | CF$_3$ | H | H | H | 2-thienyl | |
| 48 | Cl | OCHF$_2$ | H | H | H | 2-thienyl | 88.5–89° C. |
| 49 | Cl | SCHF$_2$ | H | H | H | 2-thienyl | |
| 50 | Br | OCF$_3$ | H | H | H | 2-thienyl | 107.5–108.5° C. |
| 51 | Br | OCF$_3$ | H | CH$_3$ | H | 2-thienyl | 95–98° C. |
| 52 | Br | OCF$_3$ | H | CH$_3$ | CH$_3$ | 2-thienyl | $n_D^{20}$1.5532 |
| 53 | Cl | CF$_3$ | H | H | H | 3-thienyl | 139–140° C. |
| 54 | Cl | OCF$_3$ | H | H | H | 3-thienyl | 105–108° C. |
| 55 | Cl | SCF$_3$ | H | H | H | 3-thienyl | 122–124° C. |
| 56 | Cl | CF$_3$ | H | CH$_3$ | H | 3-thienyl | 111–112° C. |
| 57 | Cl | OCF$_3$ | H | CH$_3$ | H | 3-thienyl | 73–75.5° C. |
| 58 | Cl | SCF$_3$ | H | CH$_3$ | H | 3-thienyl | 108–110° C. |
| 59 | Cl | CF$_3$ | H | CH$_3$ | CH$_3$ | 3-thienyl | 67–69° C. |
| 60 | Cl | OCF$_3$ | H | CH$_3$ | CH$_3$ | 3-thienyl | 85–86° C. |
| 61 | Cl | SCF$_3$ | H | CH$_3$ | CH$_3$ | 3-thienyl | 100–101° C. |
| 62 | Cl | CF$_3$ | H | CH$_3$ | C$_2$H$_5$ | 3-thienyl | 118–120° C. |
| 63 | Cl | OCF$_3$ | H | CH$_3$ | C$_2$H$_5$ | 3-thienyl | 101–103° C. |
| 64 | Cl | CF$_3$ | —CH$_2$CH=CH$_2$ | CH$_3$ | CH$_3$ | 3-thienyl | viscous oil |
| 66 | Cl | CF$_3$ | —CH$_2$C≡CH | CH$_3$ | CH$_3$ | 3-thienyl | $n_D^{20}$1.5385 |
| 67 | Cl | OCF$_3$ | —CH$_2$C≡CH | CH$_3$ | CH$_3$ | 3-thienyl | $n_D^{20}$1.5351 |
| 68 | Cl | CF$_3$ | —CH$_2$C≡CH | H | H | 3-thienyl | |
| 69 | Cl | CF$_3$ | —CH$_2$C≡CH | H | CH$_3$ | 3-thienyl | |
| 70 | Cl | CF$_3$ | C$_2$H$_5$ | CH$_3$ | CH$_3$ | 3-thienyl | |
| 71 | Cl | CF$_3$ | CH$_2$CH$_2$CH$_3$ | CH$_3$ | CH$_3$ | 3-thienyl | |
| 72 | Cl | CF$_3$ | CH(CH$_3$)$_2$ | CH$_3$ | CH$_3$ | 3-thienyl | |
| 73 | Cl | CF$_3$ | —CH$_2$CH(O)CH$_2$ (epoxide) | CH$_3$ | CH$_3$ | 3-thienyl | |
| 74 | Cl | CF$_3$ | CH$_2$OCH$_3$ | CH$_3$ | CH$_3$ | 3-thienyl | |
| 75 | Cl | CF$_3$ | CH$_2$CH$_2$OCH$_3$ | CH$_3$ | CH$_3$ | 3-thienyl | |
| 76 | Cl | CF$_3$ | CH$_2$SCH$_3$ | CH$_3$ | CH$_3$ | 3-thienyl | |
| 77 | Cl | CF$_3$ | CH$_2$CH$_2$SCH$_3$ | CH$_3$ | CH$_3$ | 3-thienyl | |
| 78 | Cl | CF$_3$ | CH$_2$CO$_2$CH$_2$CH$_3$ | CH$_3$ | CH$_3$ | 3-thienyl | |
| 79 | Cl | CF$_3$ | —CH(CH$_3$)CO$_2$CH$_3$ | CH$_3$ | CH$_3$ | 3-thienyl | |
| 80 | Cl | CF$_3$ | CH$_2$CN | CH$_3$ | CH$_3$ | 3-thienyl | |
| 81 | Cl | CF$_3$ | —CH$_2$C$_6$H$_5$ | CH$_3$ | CH$_3$ | 3-thienyl | |
| 82 | Cl | CF$_3$ | —CH$_2$-C$_6$H$_4$-Cl | CH$_3$ | CH$_3$ | 3-thienyl | |
| 83 | Cl | CF$_3$ | —CH$_2$CH(O)CH$_2$ (epoxide) | H | H | 3-thienyl | |
| 84 | Cl | CF$_3$ | —CH$_2$CH=CH$_2$ | H | H | 3-thienyl | |
| 85 | Cl | CF$_3$ | CH$_2$OCH$_3$ | H | H | 3-thienyl | |
| 86 | Cl | CF$_3$ | CH$_2$SCH$_3$ | H | H | 3-thienyl | |
| 87 | Cl | CF$_3$ | CH$_3$ | H | H | 3-thienyl | |
| 88 | Cl | CF$_3$ | CH$_2$CH$_3$ | H | H | 3-thienyl | |
| 89 | Cl | CF$_3$ | CH$_2$CH$_2$CH$_3$ | H | H | 3-thienyl | |
| 90 | Cl | CF$_3$ | CH(CH$_3$)$_2$ | H | H | 3-thienyl | |
| 91 | Cl | CF$_3$ | CH$_2$CO$_2$CH$_2$CH$_3$ | H | H | 3-thienyl | |
| 92 | Cl | CF$_3$ | —CH(CH$_3$)CO$_2$CH$_3$ | H | H | 3-thienyl | |

TABLE 1-continued

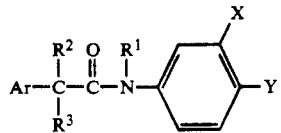

| No | X | Y | $R^1$ | $R^2$ | $R^3$ | Ar | nD or mp |
|---|---|---|---|---|---|---|---|
| 93 | F | $CF_3$ | H | H | H | 3-thienyl | |
| 94 | F | $CF_3$ | H | $CH_3$ | H | 3-thienyl | |
| 95 | F | $CF_3$ | H | $CH_3$ | $CH_3$ | 3-thienyl | |
| 96 | Cl | $OCHF_2$ | H | H | H | 3-thienyl | 85–87° C. |
| 97 | Cl | $OCHF_2$ | H | $CH_3$ | H | 3-thienyl | $n_D^{20}1.5483$ |
| 98 | Cl | $OCHF_2$ | H | $CH_3$ | $CH_3$ | 3-thienyl | $n_D^{20}1.5492$ |
| 99 | Cl | $CHF_2$ | H | H | H | 3-thienyl | |
| 100 | Cl | $CHF_2$ | H | $CH_3$ | H | 3-thienyl | |
| 101 | Cl | $CHF_2$ | H | $CH_3$ | $CH_3$ | 3-thienyl | |
| 102 | Cl | $SCHF_2$ | H | H | H | 3-thienyl | |
| 103 | Cl | $SCHF_2$ | H | $CH_3$ | H | 3-thienyl | |
| 104 | Cl | $SCHF_2$ | H | $CH_3$ | $CH_3$ | 3-thienyl | |
| 105 | Br | $OCF_3$ | H | H | H | 3-thienyl | 122–123.5° C. |
| 106 | Br | $OCF_3$ | H | $CH_3$ | H | 3-thienyl | 99–100° C. |
| 107 | Br | $OCF_3$ | H | $CH_3$ | $CH_3$ | 3-thienyl | 93–94.5° C. |
| 108 | Cl | $CH(CH_3)_2$ | H | H | H | phenyl | 193.5–96° C. |
| 109 | Cl | $CH(CH_3)_2$ | H | $CH_3$ | H | phenyl | $n_D^{20}1.5792$ |
| 110 | Cl | $CH(CH_3)_2$ | H | $CH_3$ | $CH_3$ | phenyl | 74–77° C. |
| 111 | Cl | $C(CH_3)_3$ | H | H | H | phenyl | 152.5–154° C. |
| 112 | Cl | $C(CH_3)_3$ | H | $CH_3$ | H | phenyl | 154.5–146° C. |
| 113 | Cl | $C(CH_3)_3$ | H | $CH_3$ | $CH_3$ | phenyl | 117–118° C. |
| 114 | Cl | $CH(CH_3)_2$ | H | H | H | 2-thienyl | 59–60° C. |
| 115 | Cl | $CH(CH_3)_2$ | H | $CH_3$ | H | 2-thienyl | $n_D^{20}1.5728$ |
| 116 | Cl | $CH(CH_3)_2$ | H | $CH_3$ | $CH_3$ | 2-thienyl | $n_D^{20}1.5798$ |
| 117 | Cl | $C(CH_3)_3$ | H | H | H | 2-thienyl | 117–119.5° C. |
| 118 | Cl | $C(CH_3)_3$ | H | $CH_3$ | H | 2-thienyl | 119.5–121.5° C. |
| 119 | Cl | $C(CH_3)_3$ | H | $CH_3$ | $CH_3$ | 2-thienyl | 86–88° C. |
| 120 | F | $CH(CH_3)_2$ | H | H | H | 2-thienyl | |
| 121 | F | $CH(CH_3)_2$ | H | $CH_3$ | H | 2-thienyl | |
| 122 | F | $CH(CH_3)_2$ | H | $CH_3$ | $CH_3$ | 2-thienyl | |
| 123 | Cl | $CH(CH_3)_2$ | H | H | H | 3-thienyl | $n_D^{20}1.5858$ |
| 124 | Cl | $CH(CH_3)_2$ | H | $CH_3$ | H | 3-thienyl | $n_D^{20}1.5745$ |
| 125 | Cl | $CH(CH_3)_2$ | H | $CH_3$ | $CH_3$ | 3-thienyl | 80–82.5° C. |
| 126 | Cl | $C(CH_3)_2$ | H | H | H | 3-thienyl | 119–124° C. |
| 127 | Cl | $C(CH_3)_3$ | H | $CH_3$ | H | 3-thienyl | 117–119° C. |
| 128 | Cl | $C(CH_3)_2$ | H | $CH_3$ | $CH_3$ | 3-thienyl | 85–88° C. |
| 129 | F | $CH(CH_3)_2$ | H | H | H | 3-thienyl | |
| 130 | F | $CH(CH_3)_2$ | H | $CH_3$ | H | 3-thienyl | |
| 131 | F | $CH(CH_3)_2$ | H | $CH_3$ | $CH_3$ | 3-thienyl | |
| 132 | Cl | $CH(CH_3)_2$ | H | H | H | 2-furyl | 76–78° C. |
| 133 | Cl | $CH(CH_3)_2$ | H | $CH_3$ | H | 2-furyl | |
| 134 | Cl | $CH(CH_3)_2$ | H | $CH_3$ | $CH_3$ | 2-furyl | $n_D^{20}1.5522$ |
| 135 | Br | $CH(CH_3)_2$ | H | H | H | 2-thienyl | |
| 136 | Br | $CH(CH_3)_2$ | H | $CH_3$ | H | 2-thienyl | |
| 137 | Br | $CH(CH_3)_2$ | H | $CH_3$ | $CH_3$ | 2-thienyl | |
| 138 | Br | $CH(CH_3)_2$ | H | H | H | 3-thienyl | |
| 139 | Br | $CH(CH_3)_2$ | H | $CH_3$ | H | 3-thienyl | |
| 140 | Br | $CH(CH_3)_2$ | H | $CH_3$ | $CH_3$ | 3-thienyl | |
| 141 | Cl | $CF_3$ | H | H | H | phenyl | 140–141.5° C. |
| 142 | Cl | $CF_3$ | H | $CH_3$ | H | phenyl | $n_D^{20}1.5443$ |
| 143 | Cl | $CF_3$ | H | $CH_3$ | $CH_3$ | phenyl | 199–103° C. |
| 144 | Cl | $CHF_2$ | H | H | H | phenyl | |
| 145 | Cl | $CHF_2$ | H | $CH_3$ | H | phenyl | |
| 146 | Cl | $CHF_2$ | H | $CH_3$ | $CH_3$ | phenyl | |
| 147 | Cl | $OCF_3$ | H | H | H | phenyl | 100–105° C. |
| 148 | Cl | $OCF_3$ | H | $CH_3$ | H | phenyl | $n_D^{20}1.5326$ |
| 149 | Cl | $OCF_3$ | H | $CH_3$ | $CH_3$ | phenyl | 117–118° C. |
| 150 | Cl | $OCHF_2$ | H | H | H | phenyl | 96.5–97.5° C. |
| 151 | Cl | $OCHF_2$ | H | $CH_3$ | H | phenyl | |
| 152 | Cl | $OCHF_2$ | H | $CH_3$ | $CH_3$ | phenyl | |
| 153 | Cl | $SCF_3$ | H | H | H | phenyl | 120–123° C. |
| 154 | Cl | $SCF_3$ | H | $CH_3$ | H | phenyl | $n_D^{20}1.5611$ |
| 155 | Cl | $SCF_3$ | H | $CH_3$ | $CH_3$ | phenyl | 130–133° C. |
| 156 | Cl | $SCHF_2$ | H | H | H | phenyl | |
| 157 | Cl | $SCHF_2$ | H | $CH_3$ | H | phenyl | |
| 158 | Cl | $SCHF_2$ | H | $CH_3$ | $CH_3$ | phenyl | |
| 159 | F | $CF_3$ | H | H | H | phenyl | |
| 160 | F | $CF_3$ | H | $CH_3$ | H | phenyl | |
| 161 | F | $CF_3$ | H | $CH_3$ | $CH_3$ | phenyl | |
| 162 | F | $CHF_2$ | H | H | H | phenyl | |
| 163 | F | $CHF_2$ | H | $CH_3$ | H | phenyl | |
| 164 | F | $CHF_2$ | H | $CH_3$ | $CH_3$ | phenyl | |
| 165 | F | $OCF_3$ | H | H | H | phenyl | |
| 166 | F | $OCF_3$ | H | $CH_3$ | H | phenyl | |

TABLE 1-continued $$Ar-\underset{R^3}{\underset{|}{C}}-\underset{\underset{R^1}{|}}{\overset{O}{\overset{\|}{C}}}-\underset{\underset{}{}}{N}-\underset{}{\overset{X}{\underset{Y}{\bigcirc}}}$$

| No | X | Y | R¹ | R² | R³ | Ar | nD or mp |
|---|---|---|---|---|---|---|---|
| 167 | F | OCF$_3$ | H | CH$_3$ | CH$_3$ | phenyl | |
| 168 | F | OCHF$_2$ | H | H | H | phenyl | |
| 169 | F | COHF$_2$ | H | CH$_3$ | H | phenyl | |
| 170 | F | OCHF$_2$ | H | CH$_3$ | CH$_3$ | phenyl | |
| 171 | F | SCF$_3$ | H | H | H | phenyl | |
| 172 | F | SCF$_3$ | H | CH$_3$ | H | phenyl | |
| 173 | F | SCF$_3$ | H | CH$_3$ | CH$_3$ | phenyl | |
| 174 | F | SCHF$_2$ | H | H | H | phenyl | |
| 175 | F | SCHF$_2$ | H | CH$_3$ | H | phenyl | |
| 176 | F | SCHF$_2$ | H | CH$_3$ | CH$_3$ | phenyl | |
| 177 | Cl | OCF$_2$CHF$_2$ | H | H | H | 2-thienyl | 89–95° C. |
| 178 | Cl | OCF$_2$CHF$_2$ | H | H | CH$_3$ | 2-thienyl | 113–114° C. |
| 179 | Cl | OCF$_2$CHF$_2$ | H | CH$_3$ | CH$_3$ | 2-thienyl | n$_D^{20}$1.5266 |
| 180 | Cl | SCF$_2$CHF$_2$ | H | H | H | 2-thienyl | |
| 181 | Cl | SCF$_2$CHF$_2$ | H | CH$_3$ | H | 2-thienyl | |
| 182 | Cl | SCF$_2$CHF$_2$ | H | CH$_3$ | CH$_3$ | 2-thienyl | |
| 183 | Cl | SO$_2$CF$_3$ | H | CH$_3$ | CH$_3$ | 2-thienyl | |
| 184 | Cl | OCHF$_2$ | H | CH$_3$ | H | 2-thienyl | viscous oil |
| 185 | Cl | OCF$_2$CHF$_2$ | H | H | H | 3-thienyl | 74–81° C. |
| 186 | Cl | OCF$_2$CHF$_2$ | H | H | CH$_3$ | 3-thienyl | 103–106° C. |
| 187 | Cl | OCF$_2$CHF$_2$ | H | CH$_3$ | CH$_3$ | 3-thienyl | n$_D^{20}$1.5280 |
| 188 | Cl | SCF$_2$CHF$_2$ | H | H | H | 3-thienyl | |
| 189 | Cl | SCF$_2$CHF$_2$ | H | H | CH$_3$ | 3-thienyl | |
| 190 | Cl | SCF$_2$CHF$_2$ | H | CH$_3$ | CH$_3$ | 3-thienyl | |
| 191 | Br | OCH$_3$ | H | H | H | phenyl | 113–120° C. |
| 192 | Br | OCF$_3$ | H | CH$_3$ | H | phenyl | |
| 193 | Br | OCF$_3$ | H | CH$_3$ | CH$_3$ | phenyl | |
| 194 | Cl | OCF$_2$CHF$_2$ | H | H | H | phenyl | 98–104° C. |
| 195 | Cl | OCF$_2$CHF$_2$ | H | CH$_3$ | H | phenyl | |
| 196 | Cl | OCF$_2$CHF$_2$ | H | CH$_3$ | CH$_3$ | phenyl | |
| 197 | Cl | SCF$_2$CHF$_2$ | H | H | H | phenyl | 120–123° C. |
| 198 | Cl | SCF$_2$CHF$_2$ | H | CH$_3$ | H | phenyl | n$_D^{20}$1.5661 |
| 199 | Cl | SCF$_2$CHF$_2$ | H | CH$_3$ | CH$_3$ | phenyl | 130–1332° C. |
| 200 | Cl | CF$_3$ | H | H | H | 2-furyl | 108–109.5° C. |
| 201 | Cl | CF$_3$ | H | CH$_3$ | CH$_3$ | 2-furyl | 72–74° C. |
| 202 | Cl | OCF$_3$ | H | H | H | 2-furyl | 100.5–102° C. |
| 203 | Cl | SCF$_3$ | H | H | H | 2-furyl | 121–122° C. |

PREPARATION EXAMPLES (INTERMEDIATES)

Example 7

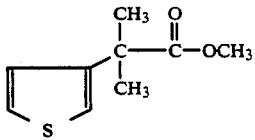

A mixture of 60% sodium hydride (29.2 g) in oil was washed with anhydrous THF to remove the oil content therefrom. Then, to the resulting sodium hydride was newly added THF (200 ml) and methyl iodide (106.5 g). To the resulting mixture was dropwise added a THF solution (100 ml) of 3-thiophene acetic acid methyl ester (47.5 g), while the mixture was gently refluxed under heating. After the dropwise addition was completed, the reaction mixture was heated under refluxing until the generation of hydrogen ceased. Then the reaction mixture was left to cool to room temperature and methanol was dropwise added to decompose unreacted sodium hydride.

Further, a small amount of acetic acid was added to the reaction mixture to decompose the sodium methoxide contained therein. Then the solvent was distilled off under reduced pressure and to the residue water was added. The aqueous layer then was extracted with ether.

The ether phase was dried over anhydrous magnesium sulfate, filtered and the solvent was distilled off by a water pump. The remaining crude product was distilled under reduced pressure to obtain 2-methyl-2-(3-thienyl) propionic acid methyl ester, bp 96°–98° C./2.0torr.

Example 8

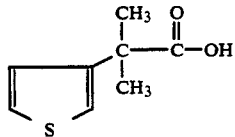

The 2-methyl-2-(3-thienyl)propionic acid methyl ester obtained in the foregoing Example 7 was added to a water:ethanol (1:4) solution (200 ml) of potassium hydroxide (18.5 g). Then the mixture was refluxed under heating for one hour and concentrated under reduced pressure, followed by a further addition of water thereto. Then the mixture was washed with dichloromethane (100 ml). The aqueous layer was acidified with diluted hydrochloric acid and the liberated carboxylic acid was extracted with dichloromethane (200 ml). The organic layer was dried over anhydrous magnesium sulfate, filtered and the solvent was removed by a water pump. The residue was recrystallized from hexane to obtain 2-methyl-2-(3-thienyl)propionic acid with mp. 78°-80.5° C.

Example 9

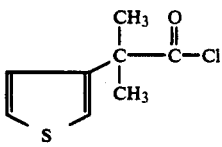

The 2-methyl-2-(3-thienyl)propionic acid (34.0 g); obtained in Example 8, was dissolved in chloroform (60 ml) and to this solution was added thionyl chloride (31.0 g), followed by a 30 minute-refluxing under heating. After the reaction, the solvent and remaining thionyl chloride was removed under reduced pressure. The remaining crude product was distilled under reduced pressure to obtain 2-methyl-2-(3-thienyl) propionic acid chloride with bp 86°-88° C./2.0torr.

Example 10

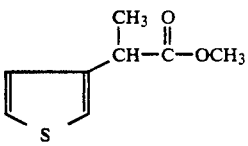

Anhydrous diisopropylamine (24.3 g) was added to Anhydrous THF (100 ml) which was then cooled by a dry ice-acetone bath. To this solution was first added dropwise n-butyllithium (15% w/o % in Hexane, 147 ml), then in a second step a THF solution (50 ml) of 3-thiophene acetic acid methyl ester (31.2 g). Thereafter, this solution was kept at the same temperature under cooling, while stirring was continued for 30 minutes. Then, methyl iodide (36.9 g) was added in one portion to the reaction mixture which after 30 minutes, was removed from the cooling bath to be allowed to reach to room temperature. After the reaction, THF was distilled off under reduced pressure and the formed residue was dissolved in water which was extracted by two portions of 200 ml ether. After the organic layer was dried over anhydrous magnesium sulfate, the solvent was evaporated under reduced pressure. The residue was purified by distillation to obtain 26.6 g 2-(3-thienyl)propionic acid methyl ester with bp 90°-92° C.

Example 11

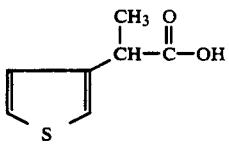

2-(3-thienyl)propionic acid methyl ester (26.6 g) was added to a water:ethanol (1:4) solution of potassium hydroxide, followed by one-hour refluxing. The reaction was carried out in a similar manner to the foregoing Example 8 to obtain 22.9 g 2-(3-thienyl) propionic acid $n_D^{20}$ 1.5361.

Example 12

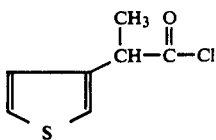

The 2-(3-thienyl)propionic acid (22.9 g) was dissolved in chloroform (60 ml), to which was added thionyl chloride (20 g), followed by 30 minutes refluxing. The reaction was carried out in a similar manner to the foregoing Example 9 to obtain 2-(3-thienyl)propionic acid chloride with bp 76°-78° C./2.0 torr.

BIOLOGICAL TEST

Comparative Compounds

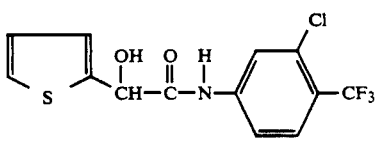

(disclosed in Japanese Laid-Open Patent Application No. 85862/1983)

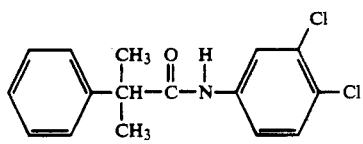

(disclosed in Japanese Laid-Open Patent Application No. 144203/1982)

Example 13

Post-emergence foliage application on upland weeds.

Formulation of Active Compounds

Carrier: 5 parts by weight of acetone

Emulsifier: 1 part by weight of benzyloxy polyglycol ether

To produce a suitable formulation of each of the active compounds, 1 part by weight of the active compound was mixed with stated amount of carrier and with the stated amount of emulsifier, and the resulting emulsifiable concentrate was diluted with water to the desired concentration.

Test Method

In a greenhouse, a number of pots, each having an area of 2000 cm², were charged with soil obtained from a cultivated field. Seeds of wheat were sown onto the soil in each of the pots. Thereafter, the surface of the soil was covered with a soil layer. The soil layer contained seeds in mixture of Barnyard grass, Green amaranth (*Amaranthus retroflexa*), Lamb's quarters (*Chenopodium album*), Polygonum blumei, and Common purslane (*Portulaca oleracea*). The thickness of the soil layer was about 1 cm.

Ten days after the seed-sowing and soil-covering when the wheat entered the early leafing stage of true leaves, predetermined dosages of the active compound formulations prepared as mentioned above were uniformly sprayed onto the foliage portions of test weeds in the respective test pots.

Three weeks after the spraying of the active compound formulations, the degree of the herbicidal effect on the weeds and the degree of the phytotoxicity on the crop were evaluated by the following percentage scale:

100%: Completely damaged

0%: No effect or no phytotoxicity.

A clearly superior activity compared with comparison substances C-1 and C-2, combined with an equally good selectivity in crop plants, is shown, in this test, for example by the compounds of the following preparation examples: 1, 2, 3, 4, 5, 6, 7, 8, 9, 25, 53, 54, 55, 56, 57, 59, 60, 61, 141, 142, 143, 147, 148, 153 and 154.

It will be understood that the specification and examples are illustrative but not limitative of the present invention and that other embodiments within the spirit and scope of the invention will suggest themselves to those skilled in the art.

What is claimed is:

1. An acetanilide of the formula

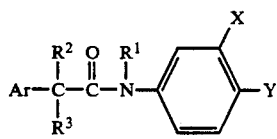

(I)

wherein

Ar represents furyl or thienyl, $R^1$ represents hydrogen, $C_{1-5}$-alkyl, $C_{3-6}$-cycloalkyl, $C_{3-6}$-cycloalkylmethyl, $C_{3-5}$-alkenyl, $C_{3-5}$-alkynyl, $C_{1-3}$-haloalkyl, $C_{3-5}$-epoxyalkyl, $C_{1-3}$-alkoxy-$C_{1-4}$-alkyl, $C_{1-3}$-alkylthio-$C_{1-4}$-alkyl, $C_{1-3}$-alkoxy-carbonyl-$C_{1-2}$-alkyl, cyano-$C_{1-3}$-alkyl, aralkyl or halogen-substituted aralkyl, $R^2$ represents hydrogen or $C_{1-3}$-alkyl, $R^3$ represents hydrogen or $C_{1-3}$-alkyl, X represents halogen, and Y represents iso-propyl, tert-butyl, $C_{1-2}$-haloalkyl, $C_{1-2}$-haloalkoxy, $C_{1-2}$-haloalkylthio or $C_{1-2}$-alkylsulfonyl.

2. A compound according to claim 1, wherein

Ar represents 2-furyl, 3-furyl, 2-thienyl, or 3-thienyl, $R^1$ represents hydrogen, $C_{1-3}$-alkyl, cyclopropyl, cyclopentyl, cyclohexyl, cyclohexylmethyl, cyclopropylmethyl, allyl, butenyl, propargyl, butynyl, halomethyl, 2,3-epoxypropyl, $C_{1-2}$-alkoxy-$C_{1-2}$-alkyl, $C_{1-2}$-alkylthio-$C_{1-2}$-alkyl, $C_{1-2}$-alkoxy-carbonyl-$C_{1-2}$-alkyl, cyano-$C_{1-2}$-alkyl or halogen-substituted benzyl, $R^2$ represents hydrogen, methyl or ethyl, $R^3$ represents hydrogen, methyl, or ethyl, X represents fluorine, chlorine or bromine, and Y represents iso-propyl, tert-butyl, $C_{1-2}$-fluoro-alkyl, $C_{1-2}$-fluoro-alkoxy, $C_{1-2}$-fluoro-alkylthio or $C_{1-2}$-fluoro-sulfonyl, with up to five fluorine atoms.

3. A compound according to claim 1, wherein

Ar represents 2-furyl, 2-thienyl or 3-thienyl, $R^1$ represents hydrogen, methyl, ethyl, n-propyl, iso-propyl, cyclopropyl, allyl, propargyl, chloromethyl, dichloromethyl, trichloromethyl, 2,3-epoxy-propyl, methoxymethyl, ethoxymethyl, methoxyethyl, methylthiomethyl, methylthioethyl, ethylthiomethyl or cyanomethyl, $R^2$ represents hydrogen or methyl, $R^3$ represents hydrogen or methyl, X represents fluorine, chlorine or bromine, and Y represents iso-propyl, tert-butyl, difluoromethyl, trifluoromethyl, difluoromethoxy, trifluoromethoxy, 1,1,2,2-tetrafluoroethoxy, difluoromethylthio, trifluoromethylthio or 1,1,2,2-tetrafluoroethylthio.

4. A compound according to claim 1, wherein

Ar represents 2- or 3-thienyl, $R^1$ represents hydrogen or methyl, $R^2$ represents hydrogen or methyl, $R^3$ represents hydrogen or methyl, X represents chlorine, and Y represents trifluoromethyl.

5. A compound according to claim 1, wherein such compound is

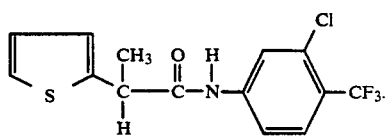

6. A compound according to claim 1, wherein such compound is

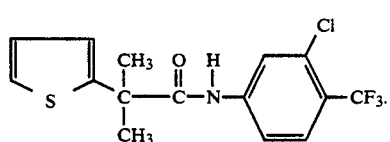

7. A compound according to claim 1, wherein such compound is

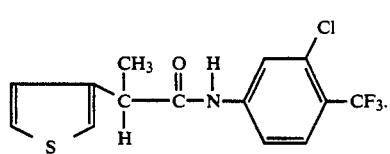

8. A compound according to claim 1, wherein such compound is

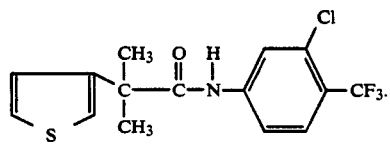

9. A herbicidal composition comprising a herbicidally effective amount of a compound according to claim 1 and a diluent.

10. A method of combating unwanted vegetation which comprises applying to such vegetation or to a locus from which it is desired to exclude such vegetation a herbicidally effective amount of a compound according to claim 1.

* * * * *